United States Patent
Ollivier et al.

(10) Patent No.: US 8,712,551 B2
(45) Date of Patent: Apr. 29, 2014

(54) MONO-BODY DEFIBRILLATION PROBE

(75) Inventors: Jean-Francois Ollivier, Villiers-le-Bacle (FR); Frederic Bessoule, Villemoisson sur Orge (FR)

(73) Assignee: Sorin CRM SAS, Clamart (FR)

( * ) Notice: Subject to any disclaimer, the term of this patent is extended or adjusted under 35 U.S.C. 154(b) by 141 days.

(21) Appl. No.: 13/004,863

(22) Filed: Jan. 11, 2011

(65) Prior Publication Data
US 2011/0185567 A1 Aug. 4, 2011

Related U.S. Application Data

(63) Continuation of application No. 11/042,797, filed on Jan. 24, 2005, now Pat. No. 7,890,189.

(30) Foreign Application Priority Data

Jan. 22, 2004 (FR) ...................... 04 00577

(51) Int. Cl.
*A61N 1/02* (2006.01)
(52) U.S. Cl.
USPC .......................... 607/122; 607/116
(58) Field of Classification Search
USPC ........................ 607/4, 5, 116, 122
See application file for complete search history.

(56) References Cited

U.S. PATENT DOCUMENTS

| 5,935,159 | A | * | 8/1999 | Cross et al. .................. 607/116 |
| 6,501,991 | B1 | | 12/2002 | Honeck et al. |
| 2001/0018607 | A1 | | 8/2001 | Borgersen et al. |
| 2004/0015221 | A1 | * | 1/2004 | Kuzma .......................... 607/116 |
| 2004/0186542 | A1 | * | 9/2004 | van Venrooij et al. ........ 607/116 |
| 2004/0230268 | A1 | | 11/2004 | Huff et al. |

\* cited by examiner

*Primary Examiner* — Tammie K Heller
(74) *Attorney, Agent, or Firm* — Foley & Lardner LLP

(57) ABSTRACT

A probe including at its distal extremity a tubular flexible sheath core supporting at least a winding forming a shock electrode and connected to an electrical conductor of connection extending in an internal lumen of the sheath core. In one embodiment of the invention, the sheath core extends axially without a solution of continuity in the area supporting the winding. In particular, the sheath core comprises cavities to receive and hold conducting inserts, of homologous size with cavities formed locally close to the ends of the winding, the insert being connected to the interior side to the electrical conductor, and on the external side to the corresponding extremity of winding. A longitudinal slit connects two cavities and allows, by elastic deformation of the sheath core, the introduction into the cavities and in the internal lumen of the unit formed by the final extremity of the electrical conductor beforehand equipped with its two inserts.

19 Claims, 4 Drawing Sheets

FIG_3

MONO-BODY DEFIBRILLATION PROBE

This application is continuation of Ser. No. 11/042,797, filed Jan. 24, 2005, now issued as U.S. Pat. No. 7,890,189, which claims priority from French Patent Application No. 04 00577, filed Jan. 24, 2005, published Apr. 21, 2006, French Publication No. 2,865,409, all of which are hereby incorporated by reference in their entirety.

FIELD OF THE INVENTION

The present invention relates to "active implantable medical devices" as defined by the Jun. 20, 1990 Directive 90/385/CEE of the Council of the European Communities.

BACKGROUND OF THE INVENTION

The invention more particularly concerns the family of apparatuses that deliver to the core pulses of high energy (i.e., pulses notably exceeding the energy provided for simple stimulation) to try to put an end to a tachyarrhythmia. These devices are called "implantable defibrillators" or "implantable cardiovertors," it being understood that the invention also covers implantable defibrillators/cardiovertors or defibrillators/cardiovertors/stimulators.

"Implantable defibrillator" or "implantable cardiovertor" devices have two principal parts—a pulse generator, and a probe or a system of probes. The pulse generator monitors cardiac activity and generates high energy pulses when the heart presents a ventricular arrhythmia that is deemed susceptible to being treated. When the high energy is comprised between approximately 0.1 and 10 J, the therapy is referred to as "cardioversion" and the electric shock is called "cardioversion shock." When the high energy is greater than approximately than 10 J, the therapy is called defibrillation and the electric shock is called "defibrillation shock." The pulse generator is connected to one or more probes comprising electrodes whose role is to distribute this energy to the core in a suitable way.

The present invention relates to the particular case where the generator is connected to a "mono-body" probe, that is a single probe carrying the various electrodes making it possible to deliver shocks of defibrillation or cardioversion. The shock electrodes appear as windings of wire supported by a distal tubular extremity of the probe and are intended to come into contact with cardiac tissues at the place where the cardioversion or defibrillation energy must be applied. The windings are connected to a conducting wire traversing the length of the probe.

Mono-body probes generally comprise two shock electrodes: a first electrode, known as "supraventricular," which will be positioned in the high vena cava to apply the shock to the atrium; and a second electrode, a ventricular one, which will be located more closely to the distal extremity of the probe.

The mono-body probes are generally of the "isodiameter" type, i.e., they have the same diameter over the entire length of the distal part intended to be implanted in the venous network. This facilitates implantation, as well as any later explantation. This means that the external surface of the windings forming the shock electrodes is flush with the external surface of the probe, so as not to present any change in diameter along the implanted length of the probe.

The manufacturing of these mono-body probes is relatively delicate, taking into account the presence of the windings, the requirements for continuity of probe diameter, and the need for carrying the electric connection inside the body of the probe with the electrical conductor allowing delivery of the shock energy.

The technique employed until now to manufacture these probes consists of taking a plurality of tubular sections of encasable sheath, one after another, setting up the windings, and electrically connecting them progressively to their internal conductor at the various sections of the tube of the probe. This structure, which makes it possible to answer the specific constraints associated with manufacturing these probes, has, however, the disadvantage of creating zones and/or electric weaknesses at the places where the various sections are connected, in particular short-circuits on the high voltage conductor supplying the shock energy. However, in practice, it has been noted that the ruptures of the insulated tube support often occur at the places of the connections between the various sections of sheath, because of the zones of weakness locally created at the place of these connections. Moreover, this structure of encased sections implies a relatively complex and long manufacturing process, in particular because of the need for sticking the successive sections together. U.S. Pat. No. 6,374,142 and PCT Application No. WO-A-02/087689 describe such mono-body isodiameter probes produced starting from encased successive sections of sheath.

OBJECTS AND SUMMARY OF THE INVENTION

One of the goals of the present invention is to cure the above-described disadvantages by proposing another structure for the distal part of a mono-body defibrillation probe—a structure that does not present a zone of weakness in the vicinity of the windings and can be manufactured simply and quickly.

The probe of the invention is a mono-body defibrillation probe of the known type described above, i.e., with a probe body that includes at its distal extremity an insulated sheath core of a tubular flexible material, supporting at its periphery at least one winding of wire forming a shock electrode for application of a defibrillation or cardioversion energy, this winding being electrically connected to an electrical conductor extending longitudinally in an internal lumen inside the sheath core.

In a manner characteristic of the invention, the sheath core extends axially without solution of continuity (i.e., without interruption) in the area(s) supporting the winding(s).

Very advantageously, the sheath core locally comprises a crossing cavity located in the vicinity of at least one of the winding ends. It is envisaged moreover that an insert of conducting material, of a size homologous with the aforesaid cavity, is placed therein, with this insert being electrically connected, on the interior side, with the electrical conductor and, on the external side, with the corresponding extremity of the winding.

In particular, the sheath core can comprise a cavity in the vicinity of each extremity of the winding, and it then comprises also a crossing longitudinal slit connecting the two cavities and radially extending from the external surface of the sheath core to the internal lumen thereof, so as to allow, by elastic strain of the material of the sheath core on both sides of the slit, the introduction into the cavities and the internal lumen of the unit formed by the final extremity of the electrical conductor provided beforehand with the two inserts to which it was mechanically and electrically connected.

In one embodiment of the invention, it is envisaged to have junction ring for mechanical and electric connection of the insert to the winding, this ring being a cylindrical ring of conducting material, with an internal surface able to cooperate with a part turned towards the outside of the insert, and an external surface comprising a connection part able to cooperate with a part turned towards the interior of the extremity of the winding. This ring can in particular comprise, in the area of internal surface able to cooperate with the insert, an assembly part capable of allowing mechanical and electric solidarization from the ring to the insert. The assembly part is preferably a part comprising a crossing opening able to allow solidarization of the ring to the insert by welding from the outside. Moreover, the diameter of the assembly part is greater than the diameter of the connection part, the difference of the diameters being approximately equal to double the thickness of the winding, so that the external surface of the ring is approximately level with the external surface of the winding.

Preferably, the probe is provided with an external envelope made of a flexible insulated material sheathing the sheath core along its length, except for the area of the winding, with the diameter of the external envelope being approximately equal to the diameter of winding. In this case, the ring can also comprise, at the opposite side of the connection part, a shafting part receiving the extremity of the external envelope adjacent to the winding. For the assembly, the insert can comprise, on the interior side, a sleeve, axially oriented, for crimping the insert to the electrical wire. Preferably both the space included between the radial walls of the slit and the internal volume of the lumen in the area of the slit are provided with an electrically insulated sealing material, such as polymeric resin that is hardenable, e.g., an adhesive silicone.

BRIEF DESCRIPTION OF THE DRAWINGS

Further benefits, features, and characteristics of the present invention will become apparent to a person of ordinary skill in the art in view of the following detailed description of a preferred embodiment of the invention, made with reference to the annexed drawings, in which like reference characters refer to like elements, and in which.

DETAILED DESCRIPTION OF THE INVENTION

Figure 1:
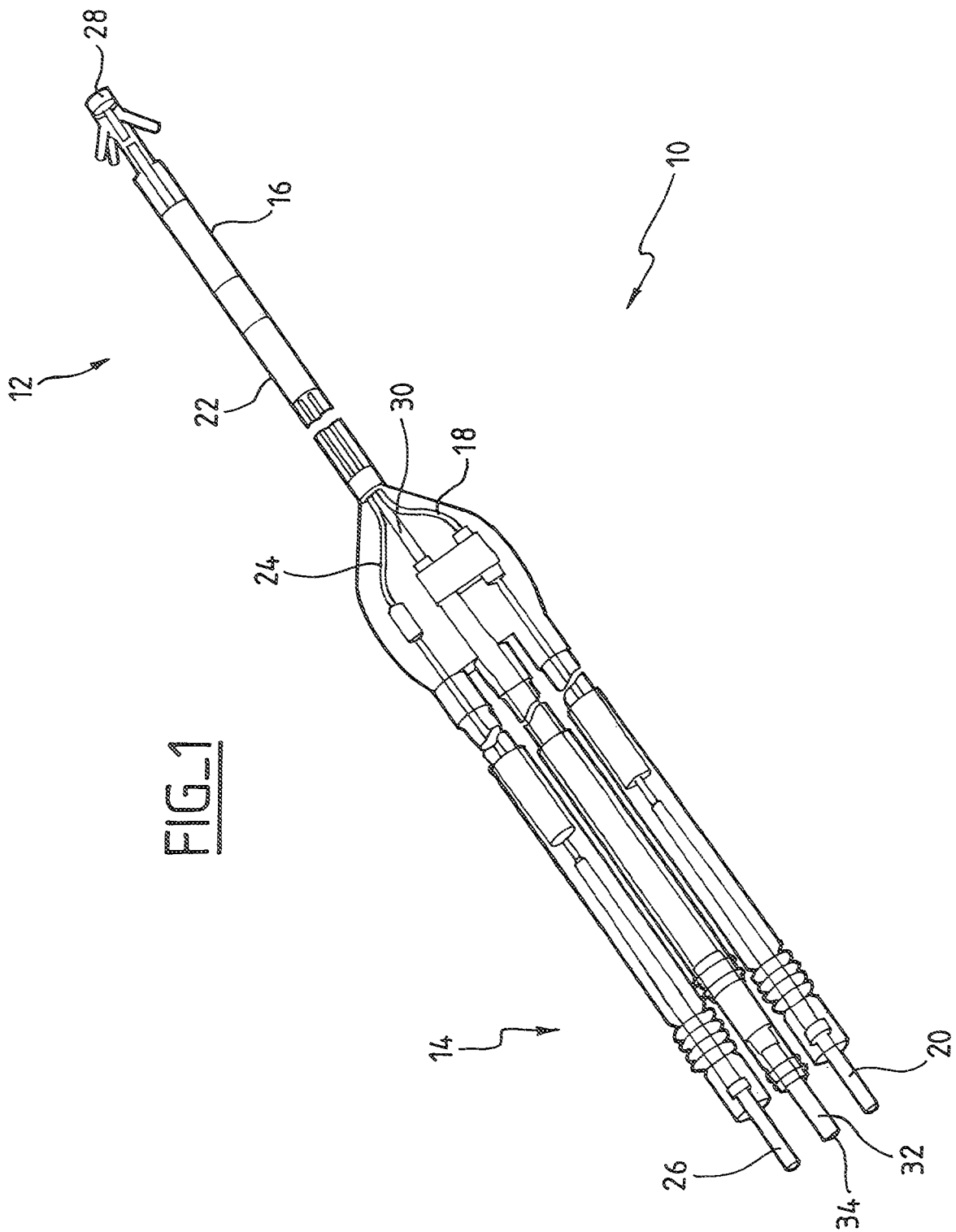
FIG. 1 is an overall view of a mono-body defibrillation probe according to the present invention.

In FIG. 1, reference 10 indicates generally a mono-body probe of which the distal extremity 12 is intended to be introduced by the venous network into the two atrial and ventricular cavities, so as to detect there cardiac activity and apply as needed a defibrillation or cardioversion shock. The probe is provided at its proximal extremity 14 with various elements for connection to an appropriate generator, e.g., a generator of the Defender or Alto or Ovatio type manufactured by the assignee hereof, ELA Medical, Montrouge, France.

Probe 10 carries a first shock electrode 16, intended to be placed in the right ventricle and constituting, e.g., the negative terminal for application of the potential voltage of defibrillation or cardioversion. This ventricular shock electrode 16 is connected by a connection conductor 18 on a connection terminal 20 to the generator, advantageously a terminal of the DF-1 standard type.

Probe 10 also carries at its distal part 12 a second shock electrode 22, which is known as a "supra-ventricular" an electrode, intended to be positioned in the high vena cava for application of a shock to the atrium. This supra-ventricular shock electrode 22 is connected by connection conductor 24 on connection terminal 26 to the generator, preferably also with a DF-1 standard connector.

Probe 10 is also equipped with an extremity electrode 28, which is a detection/stimulation electrode intended to be positioned at the bottom of the right ventricular cavity. This electrode 28 is connected by a conductor 30 on a connection terminal 32 to the pacemaker, advantageously with an IS-1 connector standard.

Figure 4:
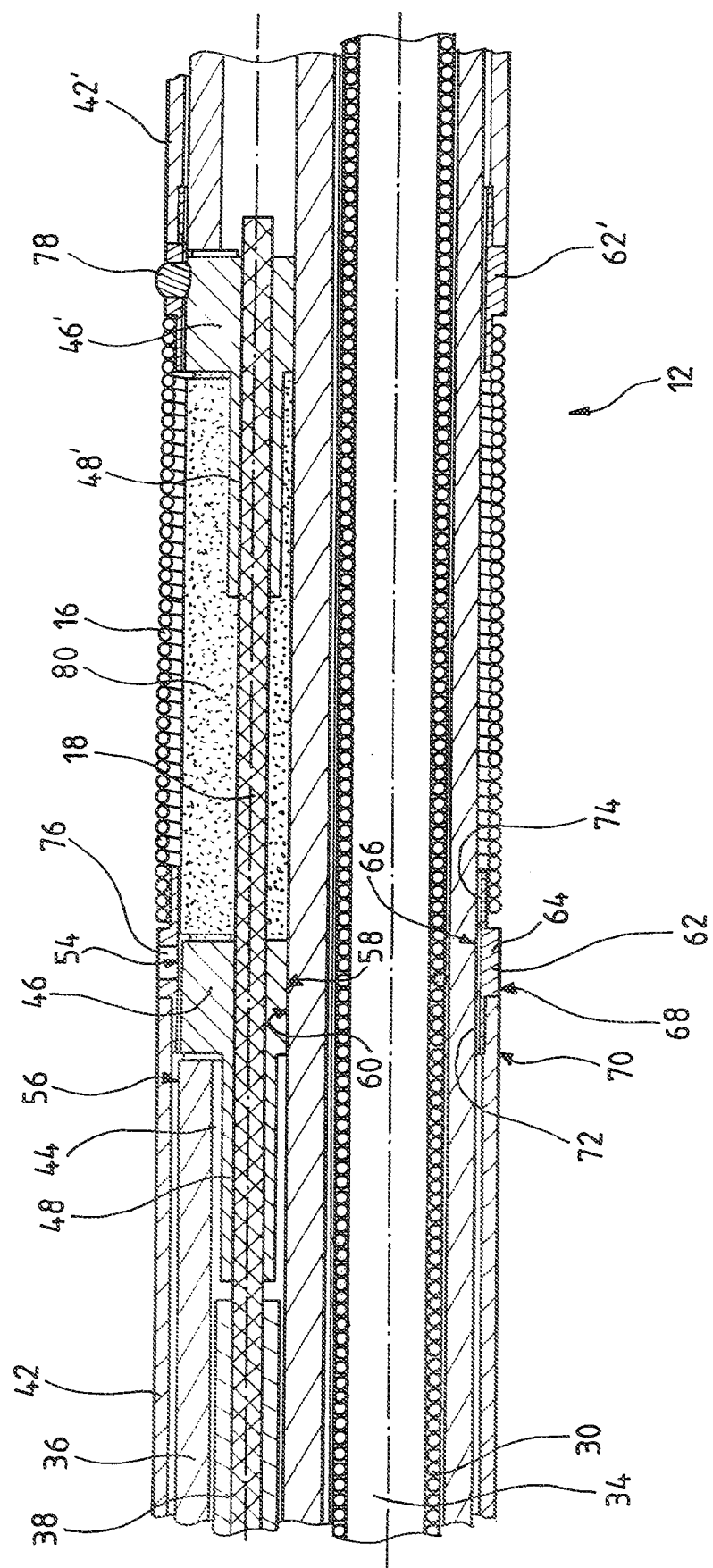
FIG. 4 is a detailed cross-section of the part of the probe at the place of the defibrillation winding, showing the various internal elements and the way that the electric connection with the winding is carried out.

As shown in FIG. 4, conductor 30 is a hollow conductor, e.g., a conductor internally wound, having in its center a lumen 34 that allows introduction of a stylet for the guidance of distal extremity 12 by a physician into the venous network at the time of implantation of the probe 10.

Referring again to FIG. 1, the defibrillation potential can be applied between the supra-ventricular shock electrode 22 and the generator case, or between the ventricular shock electrode 16 and the generator case, or between electrodes 16 and 22, in a bipolar mode.

The configuration just described (i.e., two defibrillation electrodes and one stimulation electrode) is, however, not restrictive, and the invention is also applicable to the case of a probe equipped with only one defibrillation electrode winding, or not including a distal stimulation electrode, or including two stimulation electrodes (for a stimulation in bipolar mode, in particular), etc.

Figure 2:
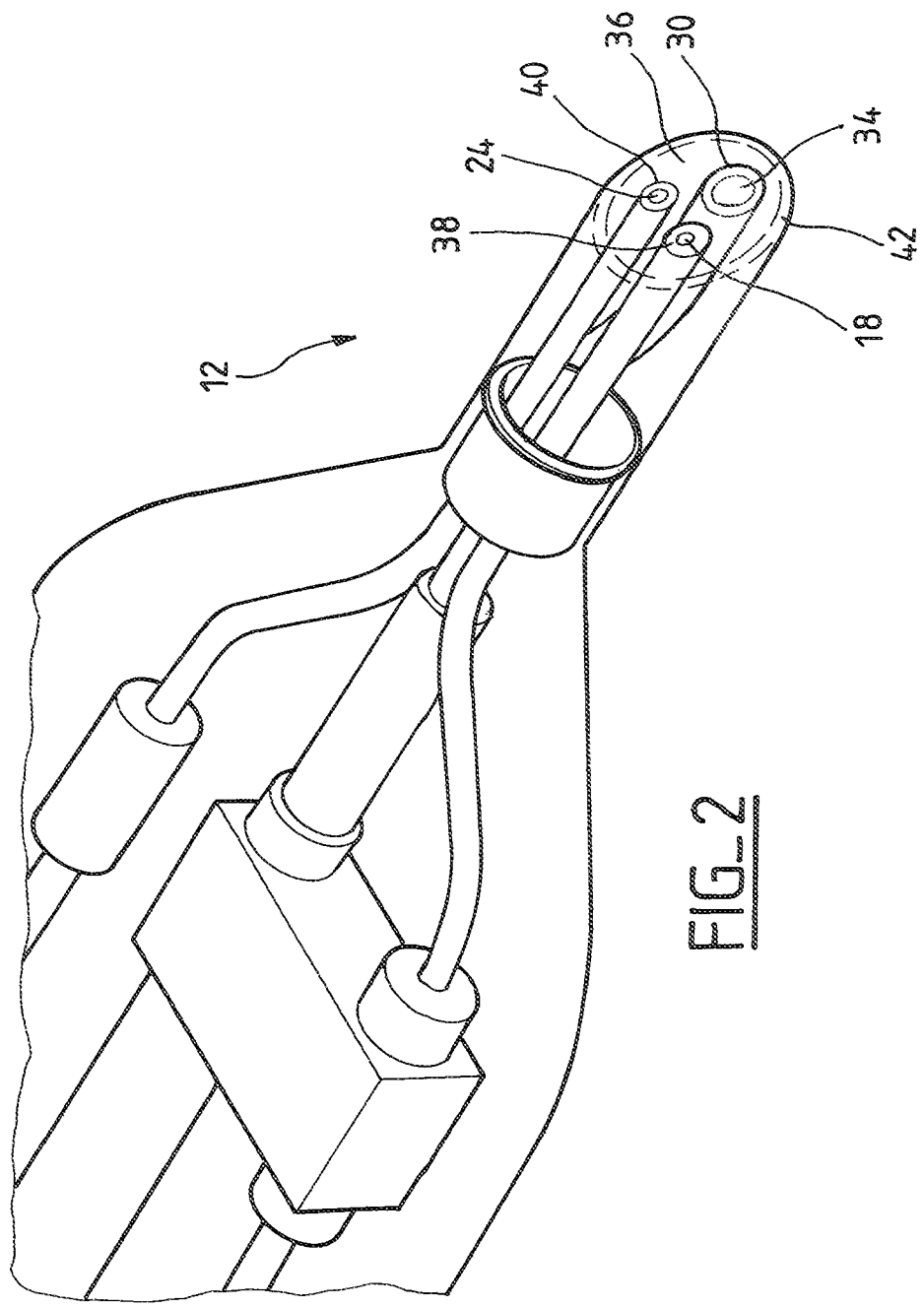
FIG. 2 is an enlarged perspective view, of the proximal extremity of the tubular sheath, at the place where the sheath terminates to widen and be divided into a plurality of conductors connected to a connector.

FIGS. 2 and 4 more precisely show the configuration of three conductors 18, 24, and 30 in the distal tubular extremity 12 of the probe 10. These conductors are placed in respective lumens of a tubular sheath core 36 made out of a flexible insulated material such as a silicone. The conductors 18 and 24, which must transmit the defibrillation or cardioversion energy, are micro-cables having their own insulators, respectively 38 and 40, e.g., in ETFE. The silicone material constituting the sheath core 36 presents excellent properties of fatigue strength. Regardless, it would be difficult to make the sheath core 36 penetrate in the venous network just as it is, and for this reason the sheath core is wrapped outside by a sheath 42 made out of a material with low coefficient of friction, e.g., polyurethane.

Figure 3:
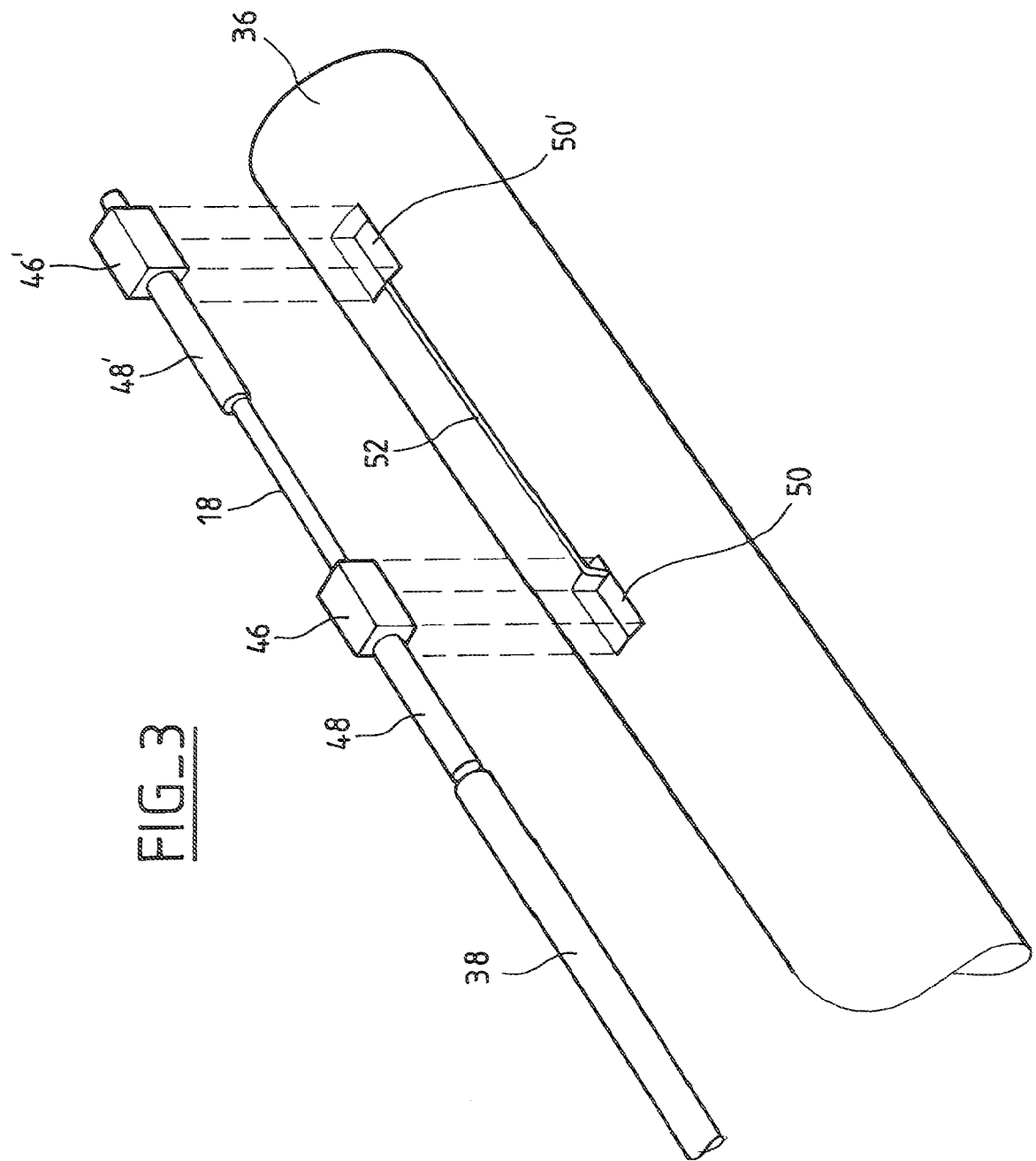
FIG. 3 is a perspective view showing the sheath core and the elements that will be there inserted to later allow connection to the defibrillation winding.

The present invention relates more particularly to the way in which the probe 10 is constructed/assembled in the vicinity of the shock electrode windings 16 and 22. FIGS. 3 and 4 illustrate a preferred structure for the ventricular shock electrode winding 16. Because this structure is the same supraventricular shock electrode winding 22, the structure for that winding will not be further described in detail.

In a way characteristic of the invention, the sheath core 36 is a solid tube, without solution of continuity over the entire length of the distal part 12, in particular in the area of the windings 16 and 22. This is due to a particular structure of the electric connection system between the winding and its corresponding conductor located inside the sheath core 36.

Thus, as illustrated in FIGS. 3 and 4, conductor 18, intended to feed the winding 16, is equipped with two metal parts 46, 46' which function as inserts, solidarized mechanically, and electrically connected, with the conductor 18 by setting of (sliding) sleeves 48, 48' over a stripped length emerging from insulator 38.

It is indeed desirable to have an electric connection of conductor 18 with the two ends of winding 16, in order to produce the most homogeneous possible electric field between these two ends at the time of application of the defibrillation or cardioversion energy. If the winding is fed by its two ends, the current density will be better distributed, thus avoiding the risk of burning the surrounding tissues. For a defibrillation shock that can require application of energy of up to 40 joules, the peak voltage can reach 750 V. For this voltage, the homogeneity of the electric field at the time of the shock is a significant constraint to take into account when designing the probe.

As illustrated in FIG. 3, the sheath core 36 comprises two cavities 50, 50', which extend from the external surface of the sheath core to the lumen 44 (FIG. 4) receiving conductor 18. These two cavities 50, 50' are joined together by a longitudinal slit 52 (FIG. 3), which extends along the sheath core 36 and radially from the external surface of the sheath core to the lumen 44 (FIG. 4) receiving conductor 18. The interior dimensions of these cavities 50, 50' are homologous with the external dimensions of inserts 46, 46', so that the inserts can be entirely placed into the cavities, with their upper surface 54 (FIG. 4) being level with the upper surface 56 of the sheath core 36. On the interior side, the lower face 58 of insert 46 preferably rests on the surface 60 of the lumen 44.

The electric and mechanical connection of inserts 46, 46', and thus of conductor 18, with winding 16, is carried out via junction rings 62, 62'. The junction ring 62 presents a central part 64, from which interior surface 66 comes in contact with the upper surface 54 of insert 46. The external surface 68 of the central part 64 has a diameter roughly equal to the external diameter of winding 16 and the external diameter of the polyurethane sheath 42; based on that, the external surface 70 of the sheath is level with the external surface 68 of the ring, thus ensuring the required isodiameter configuration. On the side that is farthest from the winding 16, ring 62 comprises a part of lesser diameter 72 intended to fix with force (friction force fit) in the interior extremity of the external sheath 42. On the side that is closest to the winding, the ring 62 comprises a part of lesser diameter 74 intended to fix with force in the interior extremity of winding 16.

To ensure the electric and mechanical solidarization of insert 46 to the connection ring of 62 (and thus winding 16), the central part 64 of the ring is equipped with an opening 76, making it possible to carry out from the outside welding point 78 (like that illustrated on the right FIG. 4), preferably a laser welding point.

Lastly, under winding 16, the remaining space around conductor 18 and around the various contiguous elements is filled with an electrically insulated sealing material, e.g., a setting polymeric resin, such as a resin silicone.

One now will describe the manner of carrying out such a probe structure with a mechanical continuity of the sheath core 36 in the area supporting the electrode.

First of all, the sheath core 36 is prepared with its external sheath 42 only in the proximal area of the probe, i.e., on the left part of FIG. 4. This external sheath thus stops in the vicinity of cavity 50 on the proximal end of the probe 16, i.e., toward the left in FIGS. 3 and 4. Separately (e.g., on another preparation setup) insulator 38 of conductor 18 is stripped on its distal side over an adaptable length, to crimp there two contact blocks 46, 46' at a desired distance, by means of sleeves 48, 48'. The unit obtained is illustrated partly on the top portion of FIG. 3. Conductor 18 is then threaded by its proximal extremity (i.e., the one opposed to the contact blocks 46, 46') into lumen 44 via opening 50 of the sheath core 36, while letting exceed on the distal side the free part with the inserts 46, 46'. The set formed by this length of wire with the inserts 46, 46' is then completely introduced inside the sheath core 36, by placing two inserts 46, 46' in the two homologous cavities 50, 50', with the part of conductor 18 connecting these two inserts being introduced by elastic deformation of sheath core material on both sides of slit 52. Once the unit is thus introduced, sleeves 48, 48' and conductor 18 find their place inside lumen 44 and the two lips of slit 52 can thus regain their initial shape. The unit is maintained tightly in place with a local injection, via slit 52, of a resin silicone mass (reference number 80 on FIG. 4), which thus comes to fill lumen 44 at the place of slit 52 and cavities 50, 50', with a tight obturation of lumen 44 on both sides of the unit thus made up.

The following stages consist of, successively:
1. slipping on the ring 62,
2. fixing the ring 62 in the part of external sheath 42 located on the proximal side of the probe (on the left on FIG. 4);
3. slipping on the winding 16;
4. fixing the proximal extremity of the winding on the ring 62;
5. slipping on the ring 62;
6. fixing the ring 62 on the distal extremity of the winding 16;
7. slipping the sheath 42' on the distal side of the probe; and
8. fixing on the ring 62'.

The unit is thus mechanically assembled. The operation is repeated identically for the other winding. Laser welding points 78 make it possible to perform the electric and mechanical connection of the rings 62, 62' on the one hand to the ends of winding 16 (in zone 74), and on the other hand to the respective inserts 46, 46'.

One skilled in the art will appreciate that the present invention can be practiced by other than the described embodiments, which are presented for purposes of illustration and not of limitation.

We claim:

1. A method of assembling a medical probe structure with mechanical continuity comprising:
   providing a mono-body sheath having a sheath core made of an elastic material, wherein the sheath core comprises an external surface, an internal surface, and an internal lumen in contact with the internal surface and extending longitudinally along a length of the sheath core, wherein the sheath core comprises a cavity extending from the external surface to the internal lumen; and
   inserting a conductor into the internal lumen of the sheath core through the cavity, wherein at least a portion of the conductor comprises an outer diameter that is larger than a corresponding portion of the cavity, and wherein inserting the conductor into the internal lumen comprises pressing the conductor against the cavity and causing a temporary elastic deformation of the elastic material of the sheath core.

2. The method of claim 1, further comprising:
   providing a winding of wire that forms one end of a shock electrode; and
   electrically connecting the conductor to said winding.

3. The method of claim 2, wherein the winding of wire is positioned proximate to the external surface of the sheath core, and wherein electrically connecting the conductor to the winding comprises connecting the inserted conductor to the winding through the cavity.

4. The method of claim 3, further comprising providing a ring comprising a conductive material, wherein connecting the inserted conductor to the winding through the cavity comprises connecting the inserted conductor and the winding to the ring.

5. The method of claim 4, wherein connecting the inserted conductor to the ring comprises welding the inserted conductor to the ring through the cavity.

6. The method of claim 2, wherein a length of the cavity is at least as long as a longitudinal length of the winding, and wherein the sheath is continuous on a portion of the sheath that does not include the cavity and is discontinuous on a portion of the sheath around which the winding is positioned.

7. The method of claim 1, further comprising inserting a sealing material into the cavity after inserting the conductor.

8. A medical probe comprising:
  a sheath having a sheath core comprising an elastic material, wherein the sheath core comprises an external surface, an internal surface, and an internal lumen in contact with the internal surface and extending longitudinally along a length of the sheath core, wherein the sheath core comprises a cavity extending from the external surface to the internal lumen; and
  a conductor configured to be inserted into the internal lumen of the sheath core, wherein at least a portion of the conductor comprises an outer diameter that is larger than a corresponding portion of the cavity, and wherein the conductor is configured to be inserted into the internal lumen by pressing the conductor against the cavity and causing a temporary elastic deformation of the elastic material of the sheath core.

9. The medical probe of claim 8, further comprising a winding of wire used to form at least a portion of a shock electrode, wherein the winding of wire is configured to be connected to the conductor through the cavity.

10. The medical probe of claim 9, further comprising a ring comprising a conductive material, wherein the ring is configured to be coupled to the winding of wire and the conductor and to electrically connect the winding of wire to the conductor.

11. The medical probe of claim 10, wherein, after the conductor is inserted into the internal lumen, the ring is configured to be welded to the conductor through the cavity.

12. The medical probe of claim 9, wherein a length of the cavity is at least as long as a longitudinal length of the winding, and wherein the sheath is continuous on a portion of the sheath that does not include the cavity and is discontinuous on a portion of the sheath around which the winding is positioned.

13. The medical probe of claim 8, further comprising a sealing material configured to be inserted into the cavity after the conductor has been inserted into the internal lumen.

14. An implantable medical device comprising:
  a generator configured to generate one or more energy pulses; and
  a probe configured to receive the energy pulses from the generator and apply the pulses to a patient, wherein the probe comprises:
    a sheath having a sheath core comprising an elastic material, wherein the sheath core comprises an external surface, an internal surface, and an internal lumen in contact with the internal surface and extending longitudinally along a length of the sheath core, wherein the sheath core comprises a cavity extending from the external surface to the internal lumen, and
    a conductor configured to be inserted into the internal lumen of the sheath core, wherein at least a portion of the conductor comprises an outer diameter that is larger than a corresponding portion of the cavity, and wherein the conductor is configured to be inserted into the internal lumen by pressing the conductor against the cavity and causing a temporary elastic deformation of the elastic material of the sheath core.

15. The implantable medical device of claim 14, wherein the probe further comprises a winding of wire used to form at least a portion of a shock electrode, wherein the winding of wire is configured to be connected to the conductor through the cavity.

16. The implantable medical device of claim 15, wherein the probe further comprises a ring comprising a conductive material, wherein the ring is configured to be coupled to the winding of wire and the conductor and to electrically connect the winding of wire to the conductor.

17. The implantable medical device of claim 16, wherein, after the conductor is inserted into the internal lumen, the ring is configured to be welded to the conductor through the cavity.

18. The implantable medical device of claim 15, wherein a length of the cavity is at least as long as a longitudinal length of the winding, and wherein the sheath is continuous on a portion of the sheath that does not include the cavity and is discontinuous on a portion of the sheath around which the winding is positioned.

19. The implantable medical device of claim 14, wherein the probe further comprises a sealing material configured to be inserted into the cavity after the conductor has been inserted into the internal lumen.

* * * * *